United States Patent
Quemin

(10) Patent No.: US 6,902,737 B2
(45) Date of Patent: Jun. 7, 2005

(54) TRANSLUCENT NANOEMULSION, PRODUCTION METHOD, AND USES THEREOF IN THE COSMETIC, DERMATOLOGICAL AND/OR OPHTHALMOLOGICAL FIELDS

(75) Inventor: Eric Quemin, Tremblay en France (FR)

(73) Assignee: L'Oreal, Clichy (FR)

( * ) Notice: Subject to any disclaimer, the term of this patent is extended or adjusted under 35 U.S.C. 154(b) by 311 days.

(21) Appl. No.: 10/182,401

(22) PCT Filed: Jan. 14, 2002

(86) PCT No.: PCT/FR02/00130

§ 371 (c)(1),
(2), (4) Date: Jul. 30, 2002

(87) PCT Pub. No.: WO02/056843

PCT Pub. Date: Jul. 25, 2002

(65) Prior Publication Data

US 2003/0087967 A1 May 8, 2003

(30) Foreign Application Priority Data

Jan. 18, 2001 (FR) ............................................. 01 00696

(51) Int. Cl.$^7$ ............................. A61K 7/00; A61K 9/00; B01F 3/08
(52) U.S. Cl. ......................... 424/401; 424/400; 516/53
(58) Field of Search ................................ 424/400, 401; 516/53

(56) References Cited

U.S. PATENT DOCUMENTS

| | | | |
|---|---|---|---|
| 4,536,519 A | 8/1985 | Suzuki et al. | |
| 5,834,013 A | * 11/1998 | Ribier et al. | ................. 424/450 |
| 6,013,270 A | 1/2000 | Fowler et al. | |
| 6,331,535 B1 | * 12/2001 | Tuloup et al. | ............... 514/182 |
| 6,335,022 B1 | * 1/2002 | Simonnet et al. | ........... 424/401 |
| 6,375,960 B1 | * 4/2002 | Simonnet et al. | ........... 424/401 |
| 6,391,287 B1 | * 5/2002 | Baldo et al. | ................... 424/59 |
| 6,464,990 B2 | * 10/2002 | Simonnet et al. | ........... 424/401 |
| 6,562,356 B2 | * 5/2003 | Verite et al. | ................. 424/401 |
| 2002/0155084 A1 | * 10/2002 | Roessler et al. | .......... 424/70.21 |

FOREIGN PATENT DOCUMENTS

| | | |
|---|---|---|
| DE | 197 07 800 | 9/1998 |
| EP | 0 347 844 | 12/1989 |
| EP | 0 705 593 | 4/1996 |
| EP | 0 728 460 | 8/1996 |
| EP | 0 968 704 | 1/2000 |

* cited by examiner

Primary Examiner—Gary L. King
Assistant Examiner—Marina Lamm
(74) Attorney, Agent, or Firm—Oblon, Spivak, McClelland, Maier & Neustadt, P.C.

(57) ABSTRACT

The nanoemulsion according to the invention comprises an oily phase dispersed in an aqueous phase, having oil globules with a number-average size less than 100 nm, characterized in that it contains a ternary surfactant system comprising:

a) a mixture of at least two nonionic surfactants comprising at least one ethoxylated fatty ester comprising 8 to 100 ethylene oxide units and at least one fatty acid ester of sorbitan; and b) at least one ionic surfactant chosen from alkali metal salts of cetyl phosphate and alkali metal salts of palmitoyl sarcosinate.

Use in the manufacture of cosmetic, dermatological and ophthalmological compositions.

34 Claims, No Drawings

TRANSLUCENT NANOEMULSION, PRODUCTION METHOD, AND USES THEREOF IN THE COSMETIC, DERMATOLOGICAL AND/OR OPHTHALMOLOGICAL FIELDS

The present invention relates to a stable translucent nanoemulsion based on a ternary system of surfactants, that does not require either the use of lower alcohols and/or of polyols, which limit the uses on sensitive skin, or of gelling agents for stabilization.

The invention also relates to a process for preparing the said nanoemulsion and to its uses in cosmetics, dermatology and/or ophthalmology. This nanoemulsion is stable on storage and can contain large amounts of oils while at the same time retaining good transparency and having good cosmetic properties.

Nanoemulsion are oil-in-water emulsions whose oil globules are of very fine particle size, that is to say that they have a number-average size of less than 100 nanometers (nm). They are generally manufactured by mechanical fragmentation of an oily phase in an aqueous phase in the presence of surfactants. In the case of nanoemulsions, the very small size of the oily globules is obtained especially by means of at least one treatment in a high-pressure homogenizer. The small size of the globules gives them cosmetically advantageous properties that distinguish them from standard emulsions: they are translucent, or even transparent, and have a novel texture. They can also convey active agents more efficiently.

Nanoemulsions comprising an amphiphilic lipid phase consisting of phospholipids, water and oil are known in the prior art. These emulsions have the drawback of being unstable on storage at the traditional storage temperatures, namely between 0 and 45° C. They lead to yellow compositions and produce rancid odours that develop after storage for a few days.

Nanoemulsions stabilized with a lamellar liquid crystal coating obtained by combining a hydrophilic surfactant and a lipophilic surfactant are also known. However, these combinations are difficult to determine. Furthermore, the nanoemulsions obtained have a waxy, film-forming feel, that is not particularly pleasant for the user.

International patent application WO 98/47464 describes a stable lotion essentially having the consistency of water, which is suitable for a spray lotion. This lotion, an emulsion homogenized at high pressure, does not require thickeners or stabilizers. The emulsion is prepared in two stages. In a first stage, a concentrated premix is formed, the emulsifiers of which are ethoxylates of stearyl alcohol. The concentrated premix is then homogenized at 1000 bar. The concentrated emulsion obtained is then diluted to 50% in water using standard mixing equipment, so as to obtain a lotion. This technique has the drawback of involving a dilution step.

If it is desired to increase the proportion of the fatty phase in an emulsion in order to approach the consistency of a gel or a cream, there do not currently exist any examples of formulations that are both translucent and consistent that do not make use of lower alcohols ($C_1$–$C_8$ alcohols) or of polyols (glycol and polyalkylene glycol) to refine the size of the oil globules in the emulsion, which does not allow them to be used for sensitive skin and with gelling agents to stabilize the systems by providing consistency.

European patent application EP-728 460 describes nanoemulsions containing two types of surfactant:
- a nonionic surfactant selected from fatty esters of polyethylene glycol or of sorbitol;
- an ionic surfactant, namely potassium dicetyl phosphate.

To obtain a transparent nanoemulsion, 5% to 20% by weight of ethanol (which is a potentially pro-irritant compound) needs to be added in order to refine the particle size of the oil globules.

Moreover, patent application EP-1 016 453 also describes a nanoemulsion containing lower alcohols or polyols (ethanol, dipropylene glycol or polyethylene glycol) to refine the particle size.

The object of the present invention is thus to provide a nanoemulsion comprising an oily phase dispersed in an aqueous phase, which is translucent.

A subject of the present invention is also a translucent nanoemulsion comprising an oily phase dispersed in an aqueous phase, which does not comprise lower alcohols and/or polyols, thus allowing it to be used on sensitive skin.

A subject of the present invention is also a nanoemulsion as defined above having the consistency of a gel or a cream and preferably not comprising gelling agents.

A subject of the present invention is also a nanoemulsion as defined above, which is stable towards maturation, even in the absence of lower alcohols and/or polyols and/or gelling agents.

According to the invention, a nanoemulsion comprising an oily phase dispersed in an aqueous phase is prepared, having oil globules with a number-average size less than 100 nm, characterized in that it contains a ternary surfactant system comprising:
a) a mixture of at least two nonionic surfactants comprising at least one ethoxylated fatty ester comprising 8 to 100 ethylene oxide units and at least one fatty acid ester of sorbitan; and
b) at least one ionic surfactant chosen from alkali metal salts of cetyl phosphate and alkali metal salts of palmitoyl sarcosinate.

The nanoemulsions according to the invention generally have a translucent to transparent appearance and possibly a faint coloration, for example a faint pinkish or bluish coloration. They generally have a turbidity ranging from 60 to 600 NTU, measured using a Hach portable turbidimeter— Model 2100P.

The oil globules in the nanoemulsions according to the invention have a number-average size of less than 100 nm and preferably from 50 to 90 nm. This globule size may be measured, for example, using a Brookhaven BI 90 machine and is determined according to the known method of "quasi-elastic light scattering". The reduction in the size of the globules makes it possible to promote the concentration of the active agents in the surface layers of the skin (vehicle effect).

The ternary surfactant system that may be used in the nanoemulsion of the invention comprises, as indicated above, a first essential constituent (a) which is a mixture of at least two nonionic surfactants comprising at least one ethoxylated fatty ester comprising 8 to 100 ethylene oxide units and at least one fatty acid ester of sorbitan.

The fatty chain of the esters in the mixture (a) generally contain from 16 to 22 carbon atoms. The fatty chain of the esters may especially be chosen from stearyl, behenyl, arachidyl, palmityl and cetyl units, and mixtures thereof such as cetearyl.

The number of ethylene oxide units ranges from 8 to 100, preferably from 10 to 80 and better still from 20 to 60. According to one particular embodiment of the invention, this number is 40.

As examples of ethoxylated fatty esters containing 40 ethylene oxide units, mention may be made of the stearic acid ester comprising 40 ethylene oxide units, such as the product sold under the name Myrj 52 (polyethylene glycol stearate 40 EO; CTFA name: PEG-40 stearate) by the company Uniqema.

An example of a fatty acid ester of sorbitan that may be mentioned is sorbitan tristearate.

Preferably, the mixture (a) of nonionic surfactants comprises an ethoxylated fatty ester, in particular PEG-40 stearate, and a sorbitan ester, in particular sorbitan tristearate.

In general, the weight ratio of the 8 to 100 EO ethoxylated fatty ester to the sorbitan ester in the mixture (a) ranges from 0.02 to 100 and preferably from 0.04 to 80.

In general, the 8 to 100 EO ethoxylated fatty ester represents 0.01% to 10% by weight, preferably from 0.1% to 5% by weight and better still from 0.5% to 3% relative to the total weight of the nanoemulsion.

The fatty acid ester of sorbitan generally represents 0.1% to 10% by weight and preferably 0.5% to 5% by weight relative to the total weight of the nanoemulsion.

The second essential constituent of the ternary surfactant system (b) comprises at least one ionic surfactant chosen from alkali metal salts of cetyl phosphate and alkali metal salts of palmitoyl sarcosinate, and mixtures thereof.

The preferred salts are potassium cetyl phosphate and sodium palmitoyl sarcosinate, and mixtures thereof.

In general, the ratio of constituent (b) to constituent (a) in the ternary surfactant system ranges from 0.02 to 75 and preferably from 0.02 to 10.

The content of ionic surfactant according to the invention can range from 0.05% to 10% by weight, preferably from 0.2% to 5% and better still from 0.5% to 3% by weight relative to the total weight of the nanoemulsion.

The nanoemulsion according to the invention comprises an oily phase. Typically, the weight ratio of the ternary surfactant system to the oily phase ranges from $6 \times 10^{-3}$ to 60 and preferably from 0.4 to 19.

Generally, the oily phase represents from 0.5% to 40% by weight and preferably from 5% to 30% by weight relative to the total weight of the nanoemulsion.

The oily phase of the nanoemulsions according to the invention contains at least one oil which may be chosen from oils of animal or plant origin, mineral oils, synthetic oils, silicone oils, hydrocarbons, especially aliphatic hydrocarbons, and mixtures thereof. These oils may be polar or non-polar, and volatile or non-volatile.

Among the polar oils that may be mentioned are hydrocarbon-based oils comprising ester, ether, acid or alcohol functions or mixtures thereof, such as, for example:

hydrocarbon-based plant oils with a high content of triglyceride, consisting of fatty acid esters and glycerol, the fatty acids of which may have varied chain lengths, the said chains possibly being linear or branched, and saturated or unsaturated; these oils are especially wheatgerm oil, corn oil, sunflower oil, karite oil, castor oil, sweet almond oil, macadamia oil, apricot oil, soybean oil, rapeseed oil, cotton oil, alfalfa oil, poppy oil, pumpkin oil, sesame oil, marrow oil, avocado oil, hazelnut oil, grapeseed oil, blackcurrant seed oil, evening primrose oil, millet oil, barley oil, quinoa oil, olive oil, rye oil, safflower oil, candlenut oil, passionflower oil, or musk rose oil, or alternatively caprylic/capric acid triglycerides, for instance those sold by the company Stearineries Dubois or those sold under the name Miglyol 810, 812 or 818 by the company Dynamit Nobel;

synthetic oils of formula $R^1COOR^2$, in which $R^1$ represents a linear or branched higher fatty acid residue containing from 7 to 19 carbon atoms and $R^2$ represents a branched hydrocarbon-based chain containing from 3 to 20 carbon atoms, such as, for example, purcellin oil (cetostearyl octanoate), isononyl isononoate or alkyl ($C_{12}$ to $C_{15}$) benzoates;

synthetic esters and synthetic ethers, for instance isopropyl myristate, 2-ethylhexyl palmitate and octanoates, decanoates or ricinoleates of alcohols or of polyalcohols;

hydroxylated esters, for instance isostearyl lactate, diisostearyl malate and pentaerythritol esters.

Among the apolar oils that may be mentioned are:

volatile or non-volatile, linear or cyclic silicone oils that are liquid at room temperature, such as polydimethylsiloxanes (PDMSs) comprising alkyl, alkoxy or phenyl groups, pendent and/or at the end of a silicone chain and containing from 2 to 24 carbon atoms; phenylsilicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates;

linear or branched hydrocarbons or fluorohydrocarbons or fluorocarbons of synthetic or mineral origin, for instance volatile oils, such as liquid paraffins (for example isoparaffins), and aliphatic hydrocarbons (for example isododecane), or non-volatile oils and derivatives thereof, petroleum jelly, polydecenes, hydrogenated polyisobutene such as parleam oil, and squalane, and mixtures thereof.

The preferred apolar oil is parleam oil.

The oily phase may also comprise fatty substances other than the oils mentioned above, such as one or more fatty alcohols, for instance stearyl alcohol, cetyl alcohol or behenyl alcohol, fatty acids such as stearic acid, palmitic acid and behenic acid, waxes such as glyceryl mono-, di- and tripalmitostearates, and gums, and mixtures thereof.

When it is present, this other fatty substance, preferably cetyl alcohol, may represent, for example, up to 10% by weight and preferably from 2% to 5% by weight relative to the total weight of the nanoemulsion.

Although the nanoemulsions in accordance with the present invention can contain additives to improve the transparency of the formulation, such as $C_1$–$C_8$ lower alcohols, for instance ethanol, glycols such as glycerol, propylene glycol or dipropylene glycol, the nanoemulsions according to the invention are preferably free of these additives, which are generally pro-irritant.

Although the nanoemulsions according to the invention can comprise gelling agents, such as cellulose derivatives, algal derivatives, natural gums and synthetic polymers such as polycarboxyvinylic acid mixtures, the nanoemulsions according to the invention are preferably free of gelling agents of this type.

The nanoemulsions according to the invention generally have the consistency of a gel or a cream. The viscosity of the nanoemulsions in accordance with the invention generally ranges from 1 to 30 poises (=0.1 to 3 Pa.s) and preferably from 5 to 20 poises (=0.5 to 2 Pa.s), these viscosities being measured at 25° C. with a Rheomat 180 viscometer (spindle 3).

The nanoemulsions according to the invention may also comprise the additives conventionally used in cosmetology, such as preserving agents, for instance alkylparabens, fragrances and pigments, in particular for use as make-up, foundation, eyeliner, etc.

The nanoemulsions of the invention retain excellent stability after two months of accelerated ageing at 4° C., at room temperature and at 45° C.

The nanoemulsions defined above may be used in any field in which this type of composition is useful. They may especially constitute compositions for topical use, especially cosmetic and dermatological compositions. They may also be used as ophthalmic supports. They may also constitute in the pharmaceutical field a composition that may be administered orally, parenterally or transcutaneously.

Another subject of the invention thus consists of a composition for topical use, characterized in that it contains a nanoemulsion as defined above.

A subject of the invention is also an ophthalmic support, characterized in that it contains a nanoemulsion as defined above.

The nanoemulsions of the invention may contain water-soluble or liposoluble active agents with cosmetic, dermatological or ophthalmological activity.

The liposoluble active agents are in the oily globules of the emulsion, whereas the water-soluble active agents are in the aqueous phase of the emulsion. Examples of active agents that may be mentioned include vitamins, such as vitamin E, vitamin C, vitamin A and vitamin PP and derivatives thereof, and in particular esters thereof, provitamins such as panthenol, wetting agents and sunscreens.

Examples of ophthalmic active agents that may be mentioned include anti-glaucoma agents such as betaxolol; antibiotics such as acyclovir; anti-allergic agents; anti-inflammatory agents such as ibuprofen and its salts, diclofenac and its salts, and indomethacin; antiviral agents.

A subject of the invention is also a process for preparing a nanoemulsion as defined above, which process consists in mixing together the aqueous phase and the oily phase, with vigorous stirring, at a temperature ranging from 60 to 95° C., and then in homogenizing at a pressure preferably ranging from $6 \times 10^7$ Pa to $18 \times 10^7$ Pa (high-pressure homogenization).

The shear preferably ranges from $2 \times 10^6$ s$^{-1}$ to $5 \times 10^8$ s$^{-1}$ and preferably from $1 \times 10^8$ s$^{-1}$ to $35 \times 10^8$ s$^{-1}$.

The nanoemulsion of the invention may be used, for example, to care for, treat or make up the skin, the face and/or the scalp.

The subject of the invention is thus also the cosmetic use of the nanoemulsion as defined above to care for, treat and/or make up the skin, the face and/or the scalp.

In addition, the nanoemulsion of the invention may also be used to care for and/or treat the hair. It gives a deposit of oil on the hair, making the hair shinier and more able to withstand styling, without making it lank. It also allows, as a pretreatment, the effects of dyeing or permanent-waving to be improved.

A subject of the invention is thus also the cosmetic use of the nanoemulsion as defined above to care for and/or treat the hair.

The nanoemulsion according to the invention especially allows good moisturization of the skin, the mucous membranes and/or the scalp and is particularly suitable for treating dry skin.

Another subject of the invention is thus a cosmetic process for caring for and/or moisturizing the skin, the mucous membranes and/or the scalp, characterized in that a nanoemulsion as defined above is applied to the skin, the mucous membranes and/or the scalp.

Finally, the invention relates to the use of the nanoemulsion according to the invention for the manufacture of a dermatological or ophthalmological composition, especially for the manufacture of a dermatological composition for treating dry skin.

The examples which follow will allow the invention to be understood more clearly, without, however, being limiting in nature. In the examples, except where otherwise mentioned, the percentages and parts are expressed on a weight basis.

The nanoemulsions of Examples 1 and 2 below were obtained by forming a coarse pre-emulsion in a rotor-stator, adding the aqueous phase A to the oily phase B, at 80° C. The premix was then treated five times in a high-pressure homogenizer (Soavi OBL 20 type) with a pressure in the first stage of 1100 bar and a pressure in the second stage of 120 bar, with cooling to 70° C. at the outlet.

EXAMPLE 1

| A | water | 72.60% |
|---|---|---|
|   | methylparaben | 0.2% |
| B | sorbitan tristearate | 0.9% |
|   | cetyl alcohol | 4% |
|   | glyceryl mono-, di-, tripalmitostearate | 3.3% |
|   | polyethylene glycol stearate (40 EO) | 2% |
|   | parleam oil | 15.95% |
|   | potassium cetyl phosphate | 0.75% |
|   | propylparaben | 0.1% |
|   | fragrance | 0.2% |

EXAMPLE 2

| A | water | 72.60% |
|---|---|---|
|   | methylparaben | 0.2% |
| B | sorbitan tristearate | 0.9% |
|   | cetyl alcohol | 4% |
|   | glyceryl mono-, di-, tripalmitostearate | 3.3% |
|   | polyethylene glycol stearate (40 EO) | 2% |
|   | parleam oil | 15.95% |
|   | sodium palmitoyl sarcosinate | 0.75% |
|   | propylparaben | 0.1% |
|   | fragrance | 0.2% |

For comparative purposes, emulsions as described above were prepared, replacing the ionic surfactants according to the invention with ionic surfactants conventionally used in cosmetics. The results are given in Table I below:

TABLE I

| Test no. | C1 | C2 | C3 | Example 1 | C4 | C5 | C6 |
|---|---|---|---|---|---|---|---|
| Ionic co-surfactant | None | Sodium dodecyl benzene-sulfonate | Potassium $C_{12}$—$C_{18}$ alkyl phosphate | Potassium cetyl phosphate | Sodium cetyl-stearyl sulfate (50/50 C16/C18) | Sodium lauryl sulfate (70/30 C12/C14) | Sodium α-olefin sulfonate (60/40 C14/C16) |

TABLE I-continued

| | | | | | | | | |
|---|---|---|---|---|---|---|---|---|
| Colour (NTU) | White | White | White | Translucent 450 NTU | White 817 NTU | White 689 NTU | White | |
| Globule size determined using a Brookhaven BI 90 machine | 174 | 87 | 100 | 50 | 61 | 59 | 67 | |
| % coarse particles | | 8 | 7 | 2 | 7 | 2 | 8 | |
| Rheological appearance | Gelled emulsion | Liquid | Liquid | Nanoemulsion | Liquid | Liquid | Liquid | |

| Test No. | C7 | Example 2 | C8 | C9 | C10 | C11 | C12 | C13 | C14 |
|---|---|---|---|---|---|---|---|---|---|
| Ionic co-surfactant | 2-octyl dodecyl sulfate | Sodium palmitoyl sarcosinate | Lauryl monophosphate (75%) | Potassium monoalkyl (C12-C13) phosphate | 2-hexyl decanol sulfate | Dimyristyl phosphate | Dicetyl phosphate | Trioleyl phosphate | Sodium lauroyl sarcosinate |
| Colour (NTU) | White | Translucent pink 417 NTU | White | White | White | White | White | White | White |
| Globule size determined using a Brookhaven BI 90 machine | 71 | 59 | 276 | 79 | 87 | 145 | 277 | 143 | 75 |
| Rheological appearance | Liquid | Nanoemulsion | Compact emulsion | Liquid | Liquid | Fluid | Compact emulsion | Gelled emulsion | Liquid |

The results of Table I show that a translucent nanoemulsion is obtained only with ionic co-surfactants according to the invention.

The transparency of the emulsions and nanoemulsions was measured by a coefficient of transmittance at 600 nm ranging from 10% to 90%, or by a turbidity ranging from 60 to 600 NTU, the turbidity being measured using a Hach portable turbidimeter—Model 2100 P (measurement at room temperature ≃25° C.).

The nanoemulsions of Examples 1 and 2 according to the invention had the consistency of a gel and were stable even after 2 months of accelerated ageing at 4° C., at room temperature and at 45° C.

These nanoemulsions were tested on a panel of 10 women with an average age of 36, who use day creams. They all found that the nanoemulsions were easy to spread and penetrated well into the skin, with a sensation of comfort and freshness developing immediately.

After application, the skin is soft, supple and moisturized. None of the women reported any discomfort.

What is claimed is:

1. A nanoemulsion comprising an oily phase dispersed in an aqueous phase, further comprising a ternary surfactant system comprising:
   a) a mixture of at least two nonionic surfactants comprising at least one ethoxylated fatty ester comprising 8 to 100 ethylene oxide units and at least one fatty acid ester of sorbitan; and
   b) at least one ionic surfactant chosen from the group consisting of alkali metal salts of cetyl phosphate and alkali metal salts of palmitoyl sarcosinate,
   wherein said nanoemulsion comprises oil globules with a number average size of less than 100 nm dispersed in said aqueous phase.

2. The nanoemulsion according to claim 1, wherein the ethoxylated fatty ester comprises from 10 to 80 ethylene oxide units.

3. The nanoemulsion according to claim 1, wherein the ethoxylated fatty ester comprises 40 ethylene oxide units.

4. The nanoemulsion according to claim 1, wherein the ethoxylated fatty ester is polyethylene glycol stearate 40 EO and the fatty acid ester of sorbitan is sorbitan tristcarate.

5. The nanoemulsion according to claim 1, wherein the ionic surfactant is chosen from the group consisting of potassium cetyl phosphate, sodium palmitoyl sarcosinate, and mixtures thereof.

6. The nanoemulsion according to claim 1, wherein the weight ratio of the ionic surfactant (b) to the mixture of nonionic surfactants (a) is: $0.02 \leq b/a \leq 75$.

7. The nanoemulsion according to claim 1, wherein the weight ratio of the ethoxylated fatty ester to the fatty acid ester of sorbitan is from 0.02 to 100.

8. The nanoemulsion according to claim 1, wherein the fatty acid ester of sorbitan is from 0.1% to 10% by weight relative to the total weight of the nanoemulsion.

9. The nanoemulsion according to claim 1, wherein the ethoxylated fatty ester is from 0.01% to 10% by weight relative to the total weight of the nanoemulsion.

10. The nanoemulsion according to claim 1, wherein the content of ionic surfactant is from 0.05% to 10% by weight relative to the total weight of the nanoemulsion.

11. The nanoemulsion according to claim 1, wherein the oily phase is from 0.5% to 40% by weight relative to the total weight of the nanoemulsion.

12. The nanoemulsion according to claim 1, wherein the oily phase comprises an oil chosen from the group consisting of oils of animal origin, oils of plant origin, mineral oils, synthetic oils, silicone oils, aliphatic hydrocarbons, and mixtures thereof.

13. The nanoemulsion according to claim 1, wherein the oily phase comprises a hydrogenated polyisobutene.

14. The nanoemulsion according to claim 13, further comprising at least one other fatty substance chosen from the group consisting of fatty alcohols, fatty acids, waxes, gums, and mixtures thereof.

15. The nanoemulsion according to claim 14, wherein the other fatty substance is up to 10% by weight relative to the total weight of the nanoemulsion.

16. The nanoemulsion according to claim 14, wherein the fatty alcohols are chosen from the group consisting of stearyl alcohol, cetyl alcohol and behenyl alcohol, and the fatty acids are chosen from the group consisting of stearic acid, palmitic acid and behenic acid.

17. The nanoemulsion according to claim 16, wherein the fatty alcohol is cetyl alcohol.

18. The nanoemulsion according to claim 14, wherein the other fatty substance is glyceryl mono-, di- or tripalmitostearate.

19. The nanoemulsion according to claim 1, further comprising a cosmetic active agent, a dermatological active agent or an ophthalmological active agent.

20. A composition for topical use, comprising the nanoemulsion according to claim 1.

21. A cosmetic process for caring for and/or moisturizing the skin, the mucous membranes and/or the scalp, comprising applying the nanoemulsion according to claim 1 to the skin, the mucous membranes and/or the scalp of a human.

22. A process for preparing a nanoemulsion according to claim 1, which comprises mixing the aqueous phase and the oily phase, with vigorous stirring, at a temperature of from 60 to 95° C., and then homogenizing at a pressure of from $6 \times 10^7$ Pa to $18 \times 10^7$ Pa.

23. The process according to claim 22, wherein the shear is from $2 \times 10^6$ s$^{-1}$ to $5 \times 10^6$ s$^{-1}$.

24. The nanoemulsion according to claim 6, wherein the weight ratio of the ionic surfactant (b) to the mixture of nonionic surfactants (a) is $0.02 \leq b/a \leq 10$.

25. The nanoemulsion according to claim 7, wherein the weight ratio of the ethoxylated fatty ester to the fatty acid ester of sorbitan is from 0.04 to 80.

26. The nanoemulsion according to claim 8, wherein the fatty acid ester of sorbitan is from 0.5% to 5% by weight relative to the total weight of the nanoemulsion.

27. The nanoemulsion according to claim 9, wherein the ethoxylated fatty ester is from 0.1% to 5% by weight relative to the total weight of the nanoemulsion.

28. The nanoemulsion according to claim 10, wherein the content of ionic surfactant is from 0.2% to 5% by weight relative to the total weight of the emulsion.

29. The nanoemulsion according to claim 11, wherein the oily phase is from 5% to 30% by weight relative to the total weight of the nanoemulsion.

30. The nanoemulsion according to claim 13, wherein the oil is parleam oil.

31. The nanoemulsion according to claim 15, wherein the other fatty substance is from 2% to 5% by weight relative to the total weight of the nanoemulsion.

32. A method for cosmetically treating the skin, said method, comprising applying the nanoemulsion according to claim 1 to the skin, the face or the scalp of a human.

33. A method for cosmetically treating the hair, said method comprising applying the nanoemulsion according to claim 1 to the hair of a human.

34. A method for manufacturing a dermatological or ophthalmological composition, said method comprising mixing the nanoemulsion according to claim 1 with a dermatological or ophthalmological composition.

* * * * *